United States Patent
Imoto

(10) Patent No.: US 10,401,293 B2
(45) Date of Patent: *Sep. 3, 2019

(54) MICROSCOPE AND MICROSCOPE OBSERVATION METHOD

(71) Applicant: OLYMPUS CORPORATION, Tokyo (JP)

(72) Inventor: Kentaro Imoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/909,203

(22) Filed: Mar. 1, 2018

(65) Prior Publication Data

US 2018/0195963 A1    Jul. 12, 2018

Related U.S. Application Data

(63) Continuation of application No. PCT/JP2015/076086, filed on Sep. 15, 2015.

(51) Int. Cl.
*G01N 21/64* (2006.01)
*G02B 21/00* (2006.01)
(Continued)

(52) U.S. Cl.
CPC ..... *G01N 21/6458* (2013.01); *G01N 21/6408* (2013.01); *G02B 21/002* (2013.01);
(Continued)

(58) Field of Classification Search
CPC ........... G01N 21/6458; G01N 21/6408; G01N 2201/06113; G01N 2021/6478;
(Continued)

(56) References Cited

U.S. PATENT DOCUMENTS 5,296,703 A    3/1994    Tsien
5,367,527 A    11/1994    Gruneisen
(Continued)

FOREIGN PATENT DOCUMENTS

JP    H10-97642 A    4/1998
JP    2005-274591 A    10/2005
(Continued)

OTHER PUBLICATIONS

Bingen, P. et al., "Parallelized STED fluorescence nanoscopy", Optics Express, vol. 19, No. 24, pp. 23716-23726.
(Continued)

*Primary Examiner* — David P Porta
*Assistant Examiner* — Gisselle Gutierrez
(74) *Attorney, Agent, or Firm* — Scully, Scott, Murphy & Presser, P.C.

(57) ABSTRACT

Provided is a microscope including: a scanner for scanning excitation light; an objective optical system that focuses the excitation light onto a sample and that collects fluorescence generated by the sample; a light-blocking member for transmitting a portion of the collected fluorescence; a detector for detecting the fluorescence; a setting unit that allows types of fluorescence having passed through the light-blocking member to be detected by the detector at different times in two types of positional relationships in which the positional relationship between the position of an opening in the light-blocking member and a focal point of the objective optical system in the sample is set to an optically conjugate positional relationship, in which in-focus fluorescence passes through the light-blocking member, and to an optically nonconjugate positional relationship; and an arithmetic operation unit for calculating the difference between fluorescence signals acquired at different times by the detector.

15 Claims, 11 Drawing Sheets

(51) Int. Cl.
*G02B 21/08* (2006.01)
*G02B 21/16* (2006.01)

(52) U.S. Cl.
CPC ..... *G02B 21/0032* (2013.01); *G02B 21/0044* (2013.01); *G02B 21/0076* (2013.01); *G02B 21/0084* (2013.01); *G02B 21/08* (2013.01); *G02B 21/16* (2013.01); *G01N 2021/6478* (2013.01); *G01N 2201/06113* (2013.01)

(58) Field of Classification Search
CPC ...... G02B 21/16; G02B 21/08; G02B 21/002; G02B 21/36
USPC ............................................ 250/459.1, 458.1
See application file for complete search history.

(56) References Cited

U.S. PATENT DOCUMENTS

| | | | |
|---|---|---|---|
| 6,094,300 | A | 7/2000 | Kashima et al. |
| 6,128,077 | A | 10/2000 | Jovin et al. |
| 6,462,345 | B1 | 10/2002 | Simon et al. |
| 6,496,267 | B1 | 12/2002 | Takaoka |
| 6,642,504 | B2 | 11/2003 | Cathey, Jr. |
| 6,867,919 | B2 | 3/2005 | Seyfried |
| 7,092,086 | B2 | 8/2006 | Knebel |
| 7,339,148 | B2 | 3/2008 | Kawano et al. |
| 2001/0012151 | A1 | 8/2001 | Knebel |
| 2006/0238745 | A1 | 10/2006 | Hashimoto et al. |
| 2007/0014001 | A1 | 1/2007 | Ujike et al. |
| 2007/0023686 | A1 | 2/2007 | Wolleschensky et al. |
| 2007/0025662 | A1 | 2/2007 | Gugel |
| 2007/0159690 | A1 | 7/2007 | Ulrich et al. |
| 2007/0290145 | A1 | 12/2007 | Viellerobe et al. |
| 2009/0021746 | A1 | 1/2009 | Toida et al. |
| 2009/0128898 | A1 | 5/2009 | Wolleschensky et al. |
| 2010/0128221 | A1 | 5/2010 | Muller et al. |
| 2011/0036996 | A1 | 2/2011 | Wolleschensky et al. |
| 2011/0109958 | A1 | 5/2011 | Yokoi |
| 2012/0098949 | A1 | 4/2012 | Knebel et al. |
| 2012/0113506 | A1 | 5/2012 | Gmitro et al. |
| 2012/0268812 | A1 | 10/2012 | Anhut et al. |
| 2013/0128346 | A1 | 5/2013 | Sanguu |
| 2017/0010453 | A1 | 1/2017 | Imoto et al. |

FOREIGN PATENT DOCUMENTS

| | | |
|---|---|---|
| JP | 2006-23387 A | 1/2006 |
| JP | 2006-317544 A | 11/2006 |
| JP | 2009-510498 A | 3/2009 |
| JP | 2010-532878 A | 10/2010 |
| JP | 2012-78802 A | 4/2012 |
| JP | 2012-208442 A | 10/2012 |
| JP | 2013-19908 A | 1/2013 |
| JP | 2013-130853 A | 7/2013 |
| JP | 2015-190992 A | 11/2015 |
| WO | WO 2011/023593 A1 | 3/2011 |
| WO | WO 2011/052248 A1 | 5/2011 |
| WO | WO 2014/110290 A1 | 7/2014 |
| WO | WO 2015/163261 A1 | 10/2015 |

OTHER PUBLICATIONS

Office Action dated May 15, 2018 received in U.S. Appl. No. 15/275,359.
Bertalmio, M., et al., "Image Inpainting", Proceeding of the 27th annual conference on computer graphics and interactive techniques, pp. 417-424.
International Search Report dated Jul. 14, 2015 issued in PCT/JP2015/061905.
International Search Report dated Dec. 22, 2015 issued in PCT/JP2015/076086.
International Search Report dated Aug. 30, 2016 issued in PCT/JP2016/065610.

MICROSCOPE AND MICROSCOPE OBSERVATION METHOD

CROSS-REFERENCE TO RELATED APPLICATIONS

This is a continuation of International Application PCT/JP2015/076086, with an international filing date of Sep. 15, 2015, which is hereby incorporated by reference herein in its entirety.

TECHNICAL FIELD

The present invention relates to a microscope and a microscope observation method.

BACKGROUND ART

There is a known microscope that, in order to avoid a difficulty in observing a sample at a depth due to out-of-focus fluorescence leaking into a confocal pinhole, discriminates out-of-focus fluorescence from in-focus fluorescence by using a separating member having a plurality of pinholes and a plurality of photodetectors (refer to, for example, Patent Literature 1).

CITATION LIST

Patent Literature

{PTL 1}
Japanese Unexamined Patent Application, Publication No. 2005-274591

SUMMARY OF INVENTION

One aspect of the present invention is a microscope including: a scanner for scanning excitation light from a light source; an objective optical system that focuses the excitation light scanned by the scanner onto a sample and that collects fluorescence generated by the sample at each scanning position; a light-blocking member that transmits a portion of the fluorescence collected by the objective optical system and that blocks another portion; a detector for detecting the fluorescence having passed through the light-blocking member; a setting unit that sets a positional relationship between the position of an opening in the light-blocking member and the focal point of the objective optical system in the sample to an optically conjugate positional relationship, in which in-focus fluorescence emitted from the focal point passes through the light-blocking member in an optical path from the sample to the detector, and to an optically nonconjugate positional relationship, in which the in-focus fluorescence does not pass through the light-blocking member, and that causes the detector to detect, at different times, types of fluorescence having passed through the light-blocking member in the set two types of positional relationships; and an arithmetic operation unit for calculating the difference between the fluorescence signals acquired by the detector at the different times.

Another aspect of the present invention is a microscope observation method for focusing, onto a sample through an objective optical system, excitation light scanned by a scanner, collecting, with the objective optical system, fluorescence generated by the sample at each scanning position, and detecting, with a detector, fluorescence having passed through a light-blocking member, the method including: a first step of detecting fluorescence with the detector in a state where the positional relationship between the position of an opening in the light-blocking member and a focal point of the objective optical system in the sample holds an optically conjugate positional relationship, in which in-focus fluorescence emitted from the focal point passes through the light-blocking member; a second step of detecting fluorescence with the detector at a different time from a time in the first step in a state where the positional relationship between the position of the opening in the light-blocking member and the focal point of the objective optical system in the sample holds an optically nonconjugate positional relationship, in which the in-focus fluorescence does not pass through the light-blocking member; and a third step of subtracting a fluorescence signal detected by the detector in the second step from a fluorescence signal detected by the detector in the first step.

DESCRIPTION OF EMBODIMENTS

A microscope 1 and a microscope observation method according to a first embodiment of the present invention will now be described with reference to the drawings.

Figure 1:
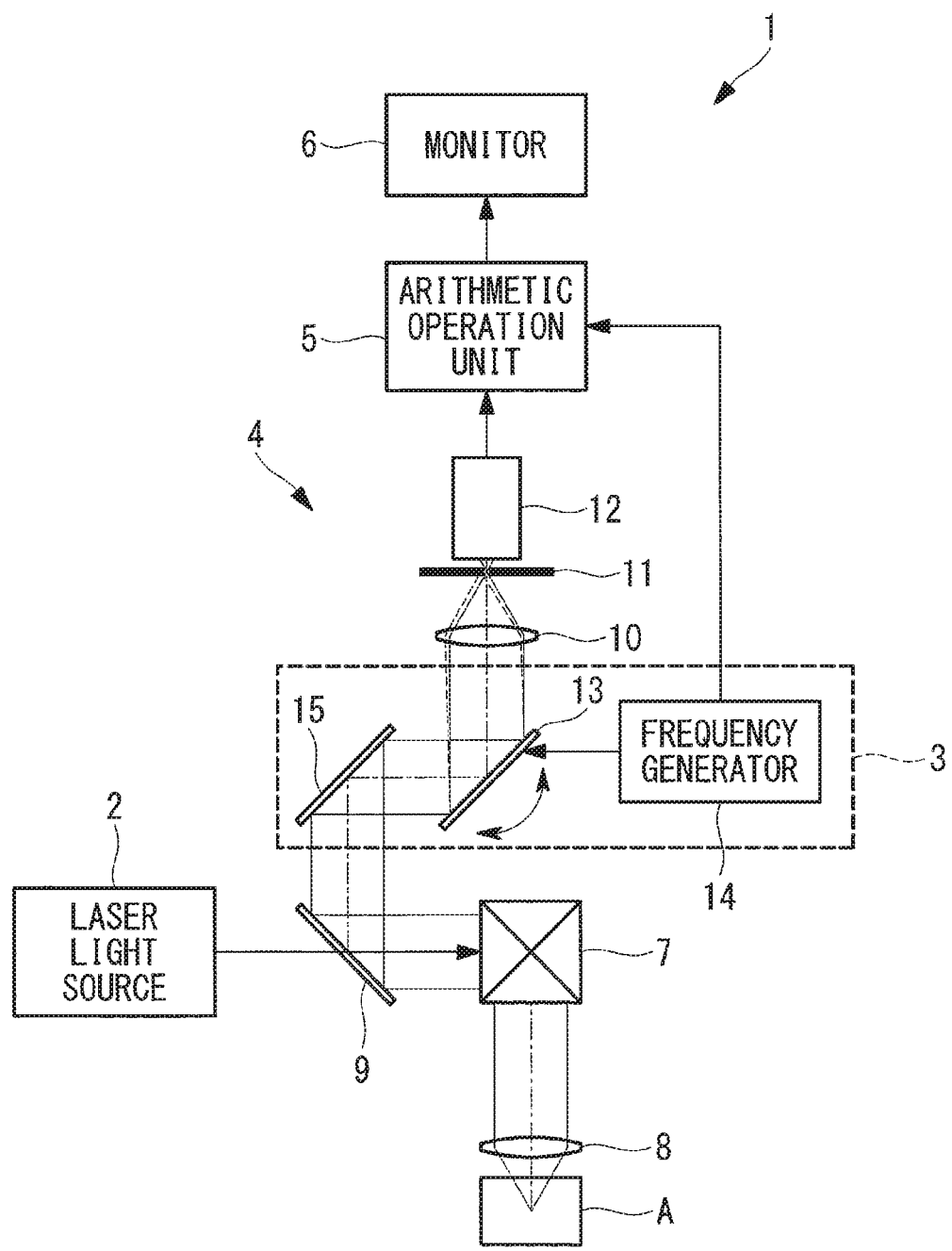
FIG. 1 is an overall configuration diagram showing a microscope according to a first embodiment of the present invention.

As shown in FIG. 1, the microscope 1 according to this embodiment includes: a microscope main body 4 that irradiates a sample A with excitation light emitted from a laser light source (light source) 2 and that detects fluorescence generated by the sample A; an arithmetic operation unit 5 for generating an image through arithmetic operation using the fluorescence detected in the microscope main body 4; and a monitor 6 for displaying the image generated by the arithmetic operation unit 5.

The microscope main body 4 includes: a scanner 7 for two-dimensionally scanning excitation light emitted from the laser light source 2; an objective lens (objective optical system) 8 that irradiates the sample A with the excitation light scanned by the scanner 7 and that collects fluorescence from the sample A; a dichroic mirror 9 for splitting off, from the optical path of the excitation light, the fluorescence that returns via the scanner 7 after being collected by the objective lens 8; a switching unit (setting unit) 3 for switching the fluorescence split off by the dichroic mirror 9 into two types; an image-forming lens 10 for focusing each type of the fluorescence switched by the switching unit 3; a pinhole (light-blocking member) 11 disposed at a position optically conjugate with the focal position of the objective lens 8; and a photodetector (detector) 12 for detecting the fluorescence that has passed through the pinhole 11.

The scanner 7 is a proximity galvanometer mirror formed by, for example, arranging, closely to each other, two galvanometer mirrors (not shown in the figure) that can swing about nonparallel axial lines. The photodetector 12 is, for example, a photomultiplier tube (PMT).

The laser light source 2 is a light source for continuously emitting excitation light.

As shown in FIG. 1, the switching unit 3 includes: a movable mirror (deflection element, light-beam moving unit) 13 that is disposed between the dichroic mirror 9 and the image-forming lens 10 and that changes the swinging angle; and a frequency generator 14 for determining the frequency at which the movable mirror 13 is driven.

In synchronization with the frequency generated by the frequency generator 14, the movable mirror 13 alternately switches the incident angle of the fluorescence, upon the image-forming lens 10, that has been split off by the dichroic mirror 9 from the optical path of the excitation light. In the figure, reference sign 15 denotes a mirror.

In this manner, the fluorescence continuously generated at a focusing point of excitation light in the sample A is alternately made incident upon the image-forming lens 10 as two types of fluorescence having different incident angles. More specifically, as shown in FIGS. 2A and 2B, the two types of fluorescence incident upon the image-forming lens 10 are formed into the shape of rectangular waves having reversed timings.

Figure 2A:
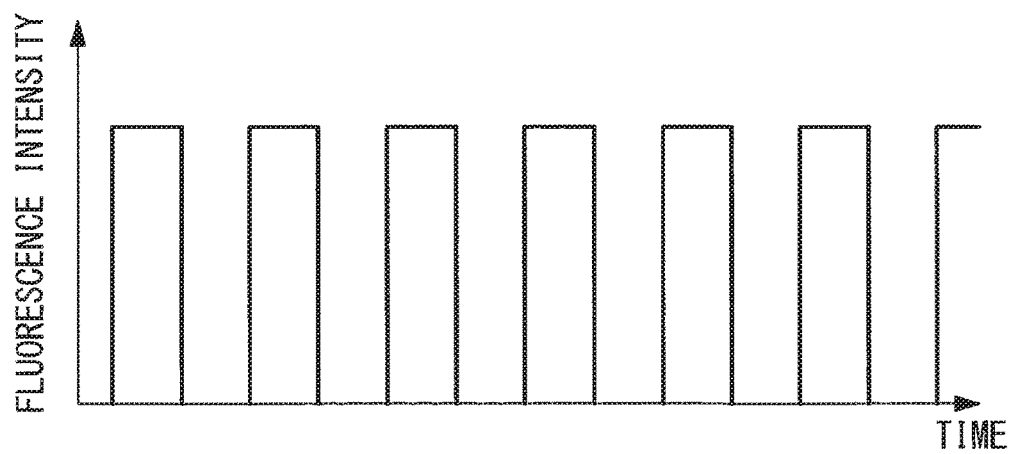
FIG. 2A is a diagram depicting one example of one type of fluorescence pattern of two types of fluorescence that have been emitted from a sample in the microscope in FIG. 1 and that have been set with a setting unit.
Figure 2B:
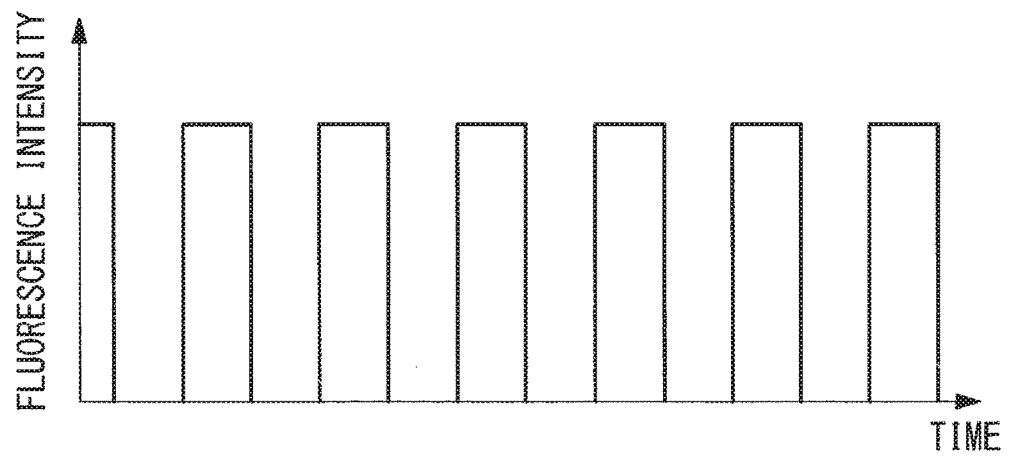
FIG. 2B is a diagram depicting one example of the other type of fluorescence pattern of two types of fluorescence that have been emitted from a sample in the microscope in FIG. 1 and that have been set with a setting unit.

One type of fluorescence shown in FIG. 2A forms a focus at a position corresponding to the pinhole 11 through the image-forming lens 10, and the other type of fluorescence shown in FIG. 2B forms a focus through the image-forming lens 10 at a position shifted relative to the pinhole 11. By doing so, the focusing point of excitation light in the sample A and the pinhole 11 have a positional relationship optically conjugate with each other in the state of FIG. 2A, whereas the focusing point of excitation light in the sample A and the pinhole 11 have a positional relationship optically nonconjugate with each other in the state of FIG. 2B. The switching frequency of the incident angle of the fluorescence upon the image-forming lens 10 is set to a frequency at which the two types of fluorescence can be blinked at least once at each pixel position.

More specifically, the fluorescence generated by irradiating the sample A with excitation light is collected by the objective lens 8, is then alternately deflected at two different angles by the movable mirror 13 constituting the switching unit 3, and is alternately detected by the photodetector 12 at different times.

The arithmetic operation unit 5 calculates the difference between the intensities of the two types of fluorescence detected by the photodetector 12 at the same pixel position.

The arithmetic operation unit 5 is composed of an electrical circuit provided with, for example, a lock-in amplifier (not shown in the figure).

The lock-in amplifier calculates, by means of hardware, the difference between the two types of fluorescence signals output from the photodetector 12 in synchronization with the frequency generated by the frequency generator 14.

The arithmetic operation unit 5 generates an image by storing the difference calculated for each pixel and the scanning position scanned by the scanner 7 such that the difference and the scanning position are associated with each other.

A microscope observation method using the microscope 1 according to this embodiment with the above-described structure will be described below.

In order to perform fluoroscopy of the sample A using the microscope 1 according to this embodiment, the sample A is placed on a stage (not shown in the figure) of the microscope main body 4, and continuous excitation light is generated by the laser light source 2 in a state where the focal position of the objective lens 8 is adjusted so as to coincide with the sample A.

Thereafter, according to a predetermined frequency generated by the frequency generator 14, the angle of the movable mirror 13 is changed in the switching unit 3.

The excitation light emitted from the laser light source 2 passes through the dichroic mirror 9, is two-dimensionally scanned by the scanner 7, and is focused onto the sample A by the objective lens 8. A portion of the fluorescence generated as a result of the sample A being irradiated with the excitation light is collected by the objective lens 8, is split off by the dichroic mirror 9 from the optical path of the excitation light on the way back via the scanner 7, and is incident upon the switching unit 3.

Because the switching unit 3 alternately switches the angle of the movable mirror 13, the portion of the fluorescence is split into two types of fluorescence in the shape of rectangular waves having reversed timings, as shown in FIGS. 2A and 2B.

Consequently, one type of fluorescence is focused onto a position coinciding with the pinhole 11, and hence the portion that has passed through the pinhole 11 is detected by the photodetector 12 (first step).

In this case, when the sample A is irradiated with excitation light, the excitation light also excites fluorescent substances on the way to the focal position of the objective lens 8 as a result of the excitation light passing through the sample A. Therefore, fluorescence is generated not only at the focal position of the objective lens 8 but also in the middle of the path to this focal position. In particular, in a case where the sample A is formed of scattering substance, fluorescence is easily generated at a site other than the focal position due to scattering of the excitation light.

In addition, particularly when the NA of the excitation light incident upon the sample A is increased in order to perform high-precision observation, the number of regions through which the excitation light passes before it reaches the focal position increases, leading to an increase in the amount of fluorescence generated at sites other than the focal position. In addition, in a case where a depth is to be observed, the number of regions through which excitation light passes also increases in the same manner, leading to an increase in the amount of out-of-focus fluorescence. Furthermore, for the purpose of observation at depth, it is necessary to increase the intensity of excitation light in order to compensate for the effect of scattering, thereby causing the effect of out-of-focus fluorescence to be particularly prominent.

Of the types of fluorescence generated by the sample A, the fluorescence generated at the focal position of the objective lens 8 is detected as signal light by the photodetector 12 since it easily passes through the pinhole 11 disposed at an optically conjugate position. However, the fluorescence generated at a site other than the focal position is scattered in the sample A, and a portion thereof passes through the pinhole 11 and is detected as noise by the photodetector 12. Therefore, the one type of fluorescence contains a fluorescence component that is generated at the focal position of the objective lens 8 and therefore should be acquired as a signal (in-focus fluorescence) and a fluorescence component that is generated at another site and therefore should not be acquired as a signal (out-of-focus fluorescence).

In addition, the in-focus fluorescence contained in the other type of fluorescence is focused onto a position shifted relative to the pinhole 11. For this reason, the in-focus fluorescence is blocked without being able to pass through the pinhole 11, whereas a portion of the out-of-focus fluorescence, which has been generated at a site other than the focal position, is scattered in the sample A, passes through the same pinhole 11, and is detected by the photodetector 12 in the same manner as in the first step (second step).

Therefore, the other type of fluorescence that has passed through the pinhole 11 contains only the out-of-focus fluorescence generated at a site other than the focal position of the objective lens 8.

Thereafter, the difference between these two types of fluorescence is calculated in the arithmetic operation unit 5 (third step). By doing so, it is possible to acquire fluorescence from which out-of-focus fluorescence, which has been generated at a site other than the focal position of the objective lens 8 and therefore should not be acquired as a signal, has been removed.

The areas in which fluorescence is generated as a result of two types of excitation light being radiated do not strictly coincide with each other. However, because those areas coincide with each other in many portions and, in addition, detection is performed by using the same pinhole 11 and photodetector 12, most of the out-of-focus fluorescence can be removed by performing subtraction as-is. In particular, when high-precision observation is to be performed by increasing the NA of excitation light, the probability that fluorescence-occurring areas overlap one another increases, hence making it possible to remove out-of-focus fluorescence even more effectively.

In this manner, the microscope 1 according to this embodiment affords an advantage in that the fluorescence generated at the focal position of the objective lens 8 can be detected with a high S/N ratio, thereby allowing acquisition of a sharp image with less noise. This advantage is particularly pronounced in the case of high-precision observation with large NA excitation light, as well as in a case where the sample A is a highly scattering substance and therefore out-of-focus fluorescence is easily generated.

This embodiment also affords an advantage in that because the difference between the two types of fluorescence acquired with an extremely short time difference is calculated for each pixel, a fluorescence image with less blurring can be acquired even in the case of the sample A moving at high speed.

Although this embodiment has been described by way of an example where the light-blocking member is realized by the pinhole 11, instead of this, an arbitrary light-blocking member may be employed, as long as the member transmits in-focus fluorescence when disposed at a position optically conjugate with the focal position of the objective lens 8 and blocks in-focus fluorescence when disposed at position nonconjugate with the focal position of the objective lens 8. Other examples of the light-blocking member include a micro mirror device and a spatial light modulator.

Figure 3:
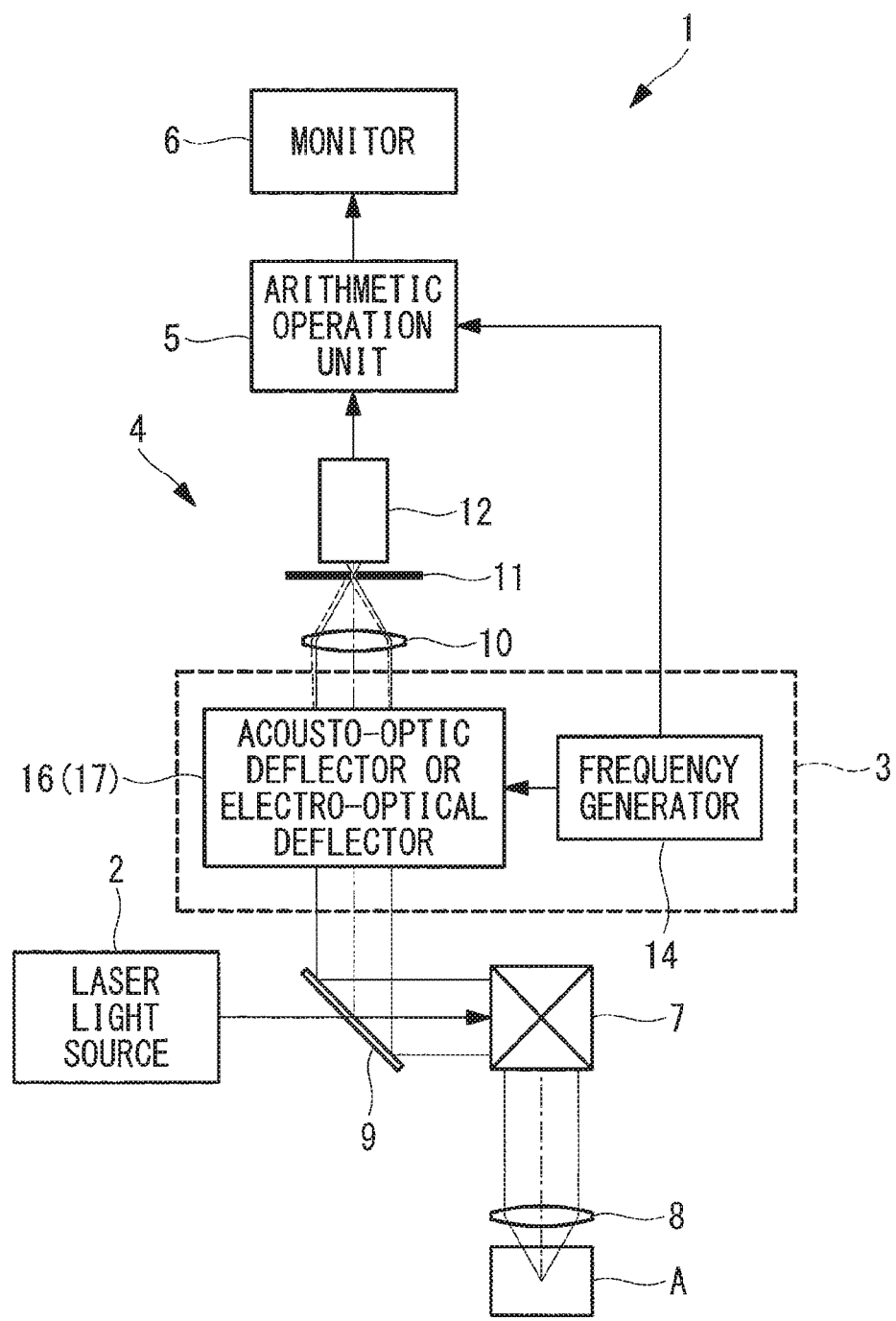
FIG. 3 is an overall configuration diagram showing a first modification of the microscope in FIG. 1.

In addition, although this embodiment has been described by way of an example where the deflection element constituting the switching unit 3 is realized by the movable mirror 13, a device, such as an acousto-optic deflector (acousto-optic element, light-beam moving unit) 16 and an electro-optical deflector (electro-optical element, light-beam moving unit) 17, can be used as shown in FIG. 3. By switching the voltage that is input according to the predetermined frequency generated by the frequency generator 14, these devices 16 and 17 can also change the incident angle of a fluorescent light beam upon the image-forming lens 10 in synchronization with the input voltage, in the same manner as with the movable mirror 13. Because these devices 16 and 17 do not include a movable part such as the movable mirror 13, they can be configured to be compact and to exhibit a long service life.

In addition, although this embodiment has been described by way of an example where the incident position of the fluorescent light beam that is incident upon the fixed light-blocking member 11 is temporally switched, the fluorescent light beam may be fixed instead, so that a light-blocking member 18 can be moved in a direction intersecting the optical axis of the fluorescent light beam.

Figure 4A:
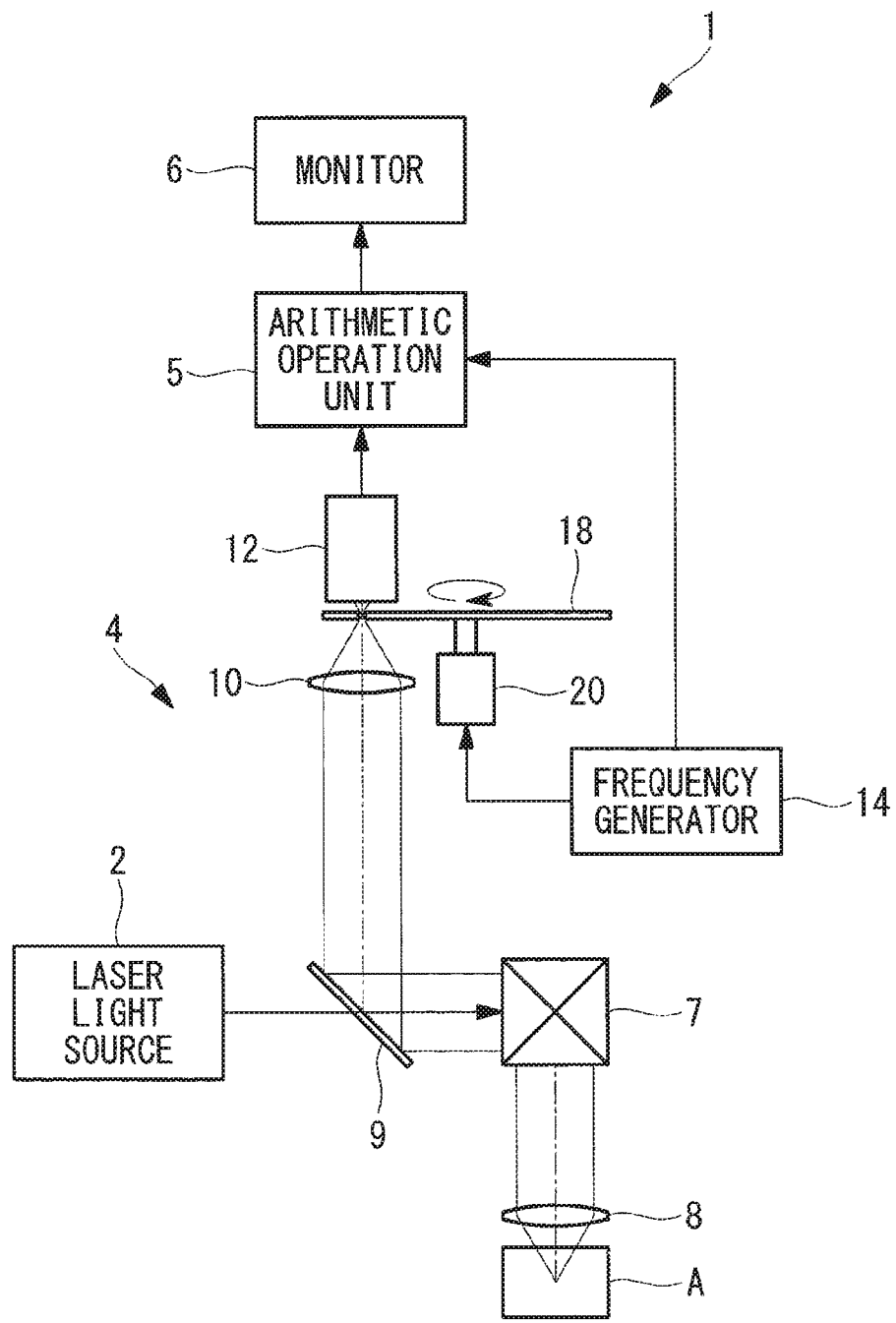
FIG. 4A is an overall configuration diagram showing a second modification of the microscope in FIG. 1.
Figure 4B:
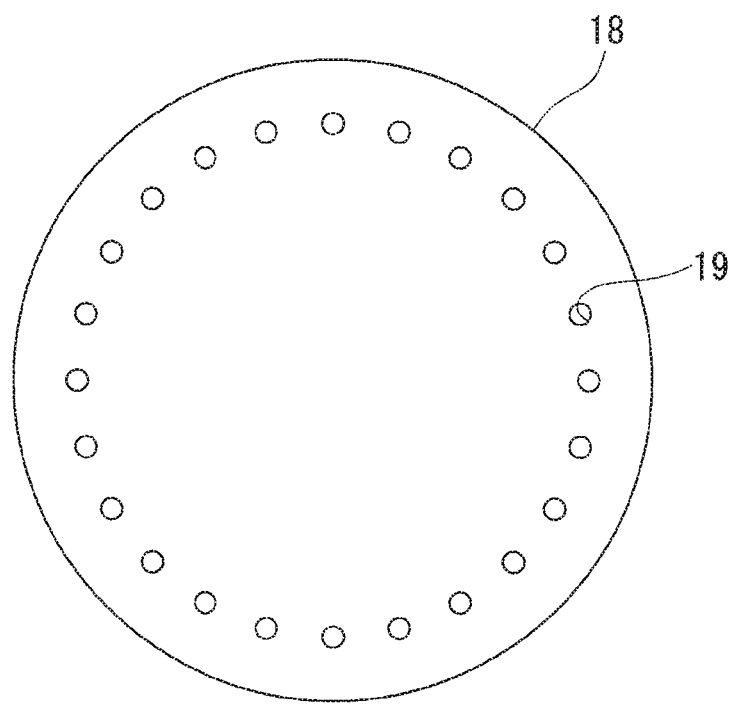
FIG. 4B is a plan view of a disc having pinholes in the microscope in FIG. 4A.

More specifically, a circular-plate-shaped disc having a plurality of pinholes 19 arranged in the circumferential direction in a manner spaced apart from each other, as shown in FIG. 4B, may be employed as the light-blocking member 18, so as to rotate the disc 18 about a central axis with a motor 20, as shown in FIG. 4A.

By doing so, in a state where the fluorescence-focusing position through the image-forming lens 10 is made to coincide with the disc 18, it is possible to alternately repeat, by rotating the disc 18 with the motor 20, a state where a pinhole 19 coincides with the optical axis of fluorescence and a state where the pinholes 19 do not coincide with the optical axis of fluorescence. More specifically, the focusing point of excitation light in the sample A and one of the pinholes 19 have a positional relationship optically conjugate with each other in a state where the pinhole 19 coincides with the optical axis of fluorescence, whereas the focusing point of excitation light in the sample A and the pinholes 19 have a positional relationship optically nonconjugate with each other in a state where none of the pinholes 19 coincide with the optical axis of fluorescence.

By doing so, an optically conjugate positional relationship and an optically nonconjugate positional relationship are formed in a temporally alternating manner, and two types of fluorescence for detecting focus fluorescence with high accuracy can be sequentially detected by the same photodetector 12. In addition, this affords an advantage in that the two positional relationships can be switched at higher speed by rotating the disc 18 at high speed.

Figure 5:
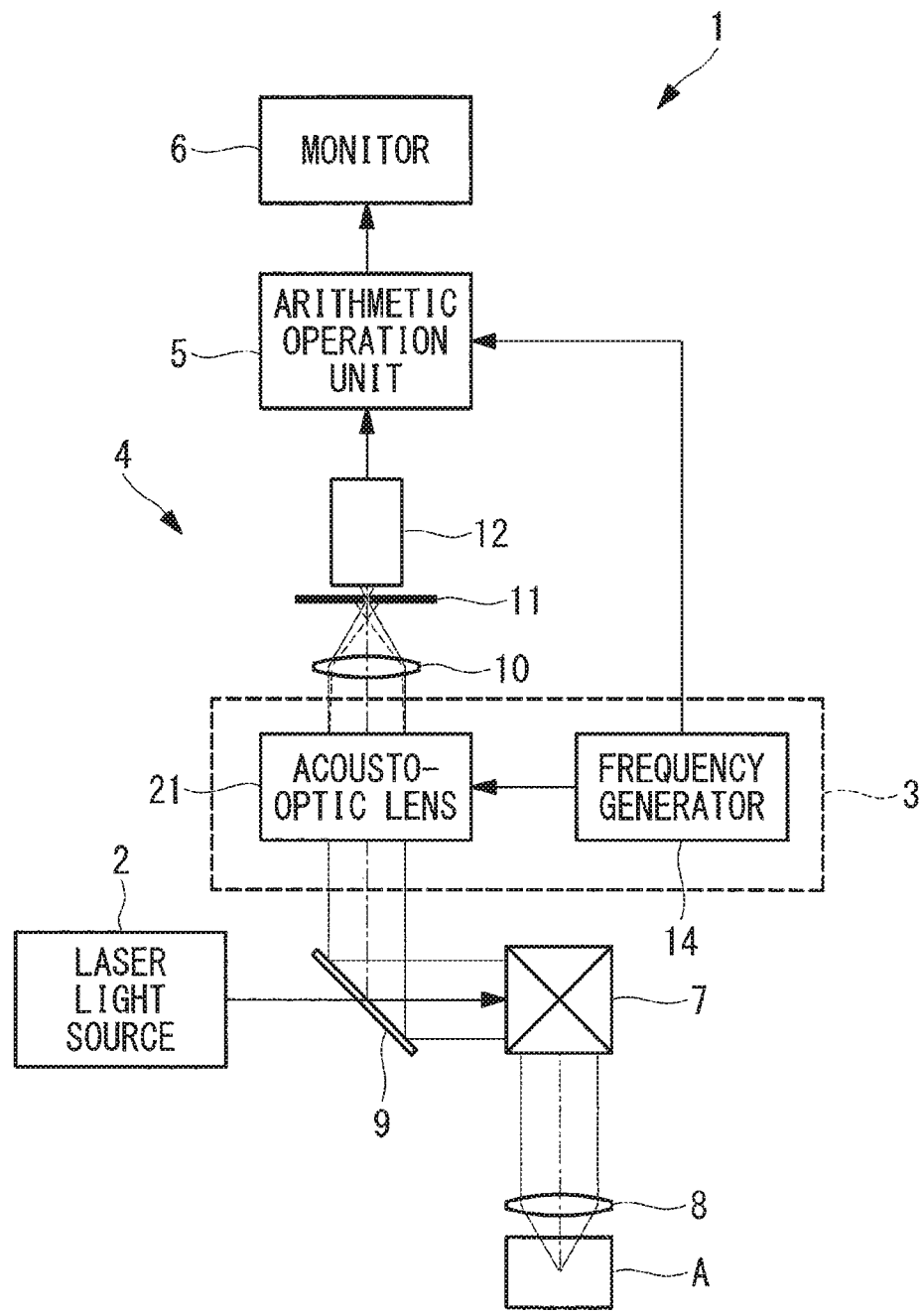
FIG. 5 is an overall configuration diagram showing a third modification of the microscope in FIG. 1.

In addition, although this embodiment has been described by way of an example where the fluorescence light beam and the pinhole 11 are relatively moved in a direction intersecting the optical axis of the fluorescence light beam, instead of this the fluorescence light beam and the pinhole 11 may be relatively moved in a direction along the optical axis of the fluorescence light beam, as shown in FIG. 5.

More specifically, in the example shown in FIG. 5, an acousto-optic lens (setting unit) 21 is employed, instead of the acousto-optic deflector 16 or the electro-optical deflector 17. The acousto-optic lens 21 is a lens for changing the refractive power according to the input voltage and can switch the image-forming position of fluorescence through the image-forming lens 10 between a position coinciding with the pinhole 11 and a position shifted from the pinhole 11 in the optical-axis direction by switching the refractive power in synchronization with the frequency based on the frequency generator 14.

By doing so, it is possible to easily switch between an optically conjugate positional relationship, in which the image-forming position of fluorescence is made to coincide with the pinhole 11, and an optically nonconjugate positional relationship, in which the image-forming position of fluorescence is shifted from the pinhole 11 in the optical-axis direction.

Next, a microscope 22 according to a second embodiment of the present invention will be described with reference to the drawings.

In explaining this embodiment, the structures in common with those used in the microscope 1 according to the first embodiment will be denoted by the same reference signs, and thus descriptions thereof will be omitted.

The microscope 22 according to this embodiment differs from the first embodiment in that the laser light source 2 emits pulse-shaped excitation light that blinks at the frequency set by the frequency generator 14 and in terms of the configuration of a switching unit (setting unit) 23.

The laser light source 2 modulates excitation light with a predetermined frequency generated by the frequency generator 14 so as to take the form of repeated waveforms as shown in FIG. 2A. The frequency of the laser light source 2 is a frequency that allows at least one cycle of excitation light to be repeated at each pixel position.

The switching unit 23 is a free-space optical system disposed between the dichroic mirror 9 and the image-forming lens 10.

Figure 6:
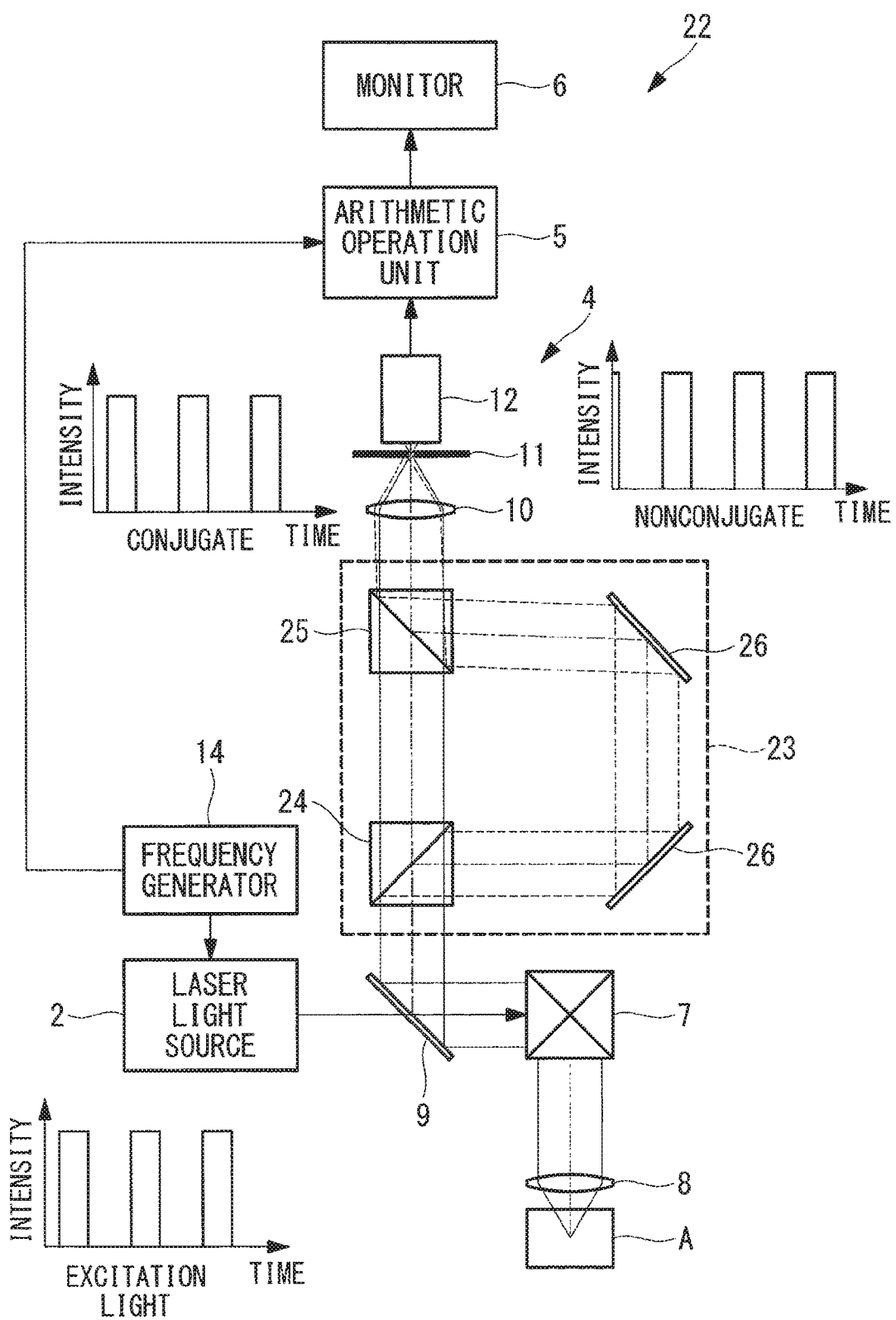
FIG. 6 is an overall configuration diagram showing a microscope according to a second embodiment of the present invention.

As shown in FIG. 6, the free-space optical system 23 includes: a first polarizing beam splitter 24 for splitting, into two optical paths, the fluorescence split-off by the dichroic mirror 9 from the optical path of the excitation light; and a second polarizing beam splitter 25 for multiplexing types of fluorescence having passed via the two optical paths.

In the example shown in FIG. 6, the fluorescence split by the first polarizing beam splitter 24 into a first optical path is incident upon the second polarizing beam splitter 25 as-is, whereas the fluorescence split into a second optical path is incident upon the second polarizing beam splitter 25 via an optical path that is formed by two optical-path forming mirrors 26 and hence that is longer than the first optical path.

In addition, the angles of the mirrors 26 are set so that the exit angle of the fluorescence emitted from the second polarizing beam splitter 25 via the first optical path differs from the exit angle of the fluorescence emitted from the second polarizing beam splitter 25 via the second optical path.

By doing so, for example, the fluorescence having passed via the first optical path forms a focus through the image-forming lens 10 at a position coinciding with the pinhole 11, and the fluorescence having passed via the second optical path forms a focus at a position shifted from the pinhole 11. Furthermore, the fluorescence having passed via the second optical path reaches the pinhole 11 at a later time than the fluorescence having passed via the first optical path, depending on the difference in optical-path length.

More specifically, the focusing point of excitation light in the sample A and the pinhole 11 have an optically conjugate positional relationship in the case of the fluorescence having passed via the first optical path and have an optically nonconjugate positional relationship in the case of the fluorescence having passed via the second optical path. Because of a delay caused by the difference in optical-path length, fluorescence detection in an optically conjugate positional relationship and fluorescence detection in an optically non-conjugate positional relationship are performed in a temporally shifted manner.

Therefore, in the same manner as in the microscope 1 according to the first embodiment, this embodiment also affords an advantage in that a sharp image from which out-of-focus fluorescence is removed can be generated by individually detecting two types of fluorescence using the same photodetector 12 and then calculating the difference between the two types of fluorescence.

Figure 7:
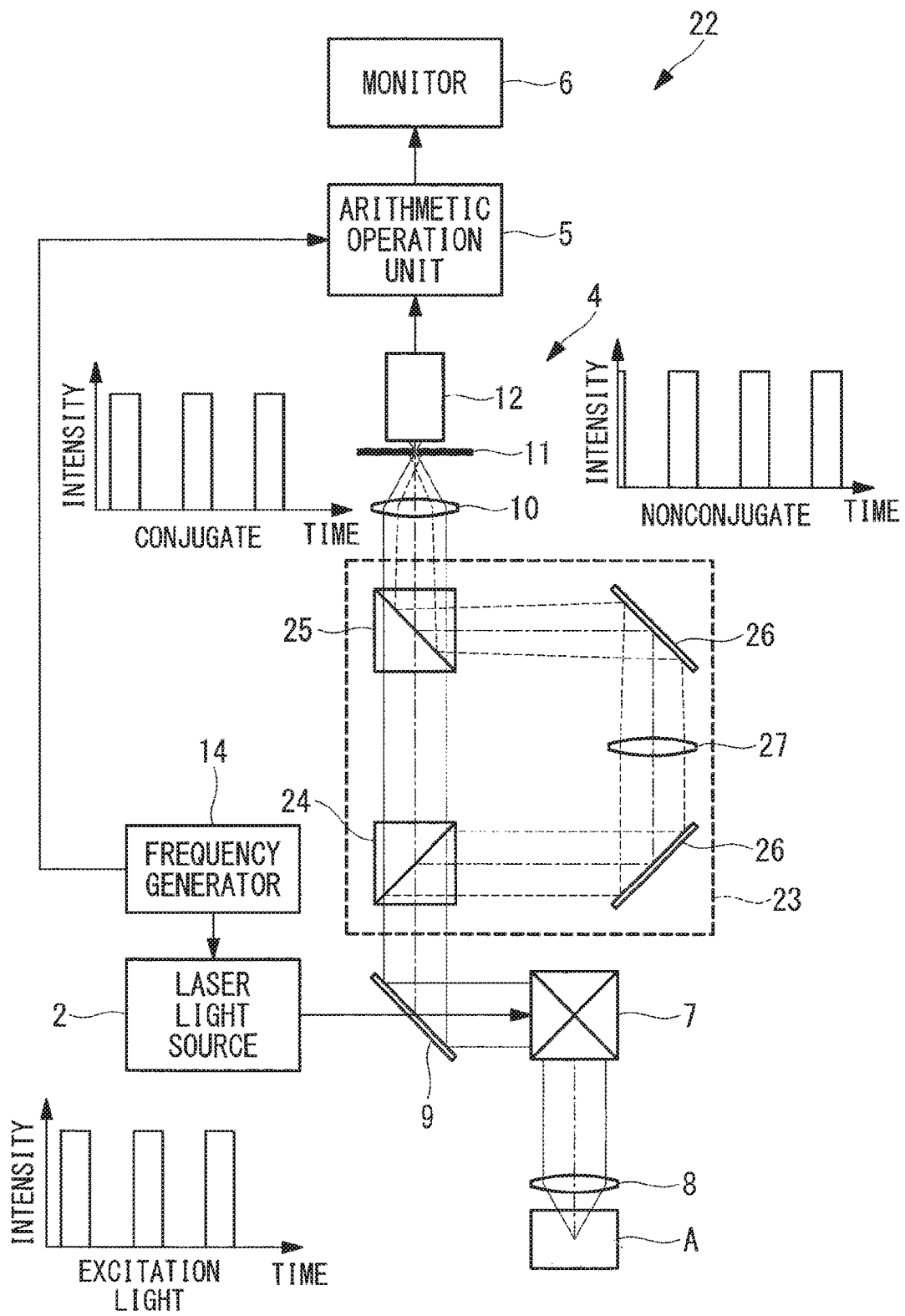
FIG. 7 is an overall configuration diagram showing a modification of the microscope in FIG. 6.

Although, in this embodiment, the image-forming positions of the two types of fluorescence are shifted in a direction intersecting the optical axis of the fluorescent light beam by adjusting the angles of the optical-path forming mirrors 26, alternatively the image-forming positions of the two types of fluorescence may be shifted in a direction along the optical axis of the fluorescent light beam by placing a lens 27 in either of the optical paths in the free-space optical system 23, as shown in FIG. 7.

In addition, although this embodiment has been described by way of an example where fluorescence is split and multiplexed by using the two polarizing beam splitters 24 and 25, instead of this an unpolarized beam splitter, such as a half mirror, may be used.

In addition, although the laser light source 2 generates excitation light shaped like rectangular waves as shown in FIG. 2A, instead of this the laser light source 2 may generate excitation light that have arbitrary repeated shapes, such as sine wave shapes, and that have different phases.

Next, a microscope 28 according to a third embodiment of the present invention will be described with reference to the drawings.

In explaining this embodiment, the structures in common with those used in the microscope 22 according to the second embodiment will be denoted by the same reference signs, and thus descriptions thereof will be omitted.

The microscope 28 according to this embodiment differs from the microscope 22 according to the second embodiment in terms of the configurations of a setting unit 29 and a light-blocking member 30.

Figure 8:
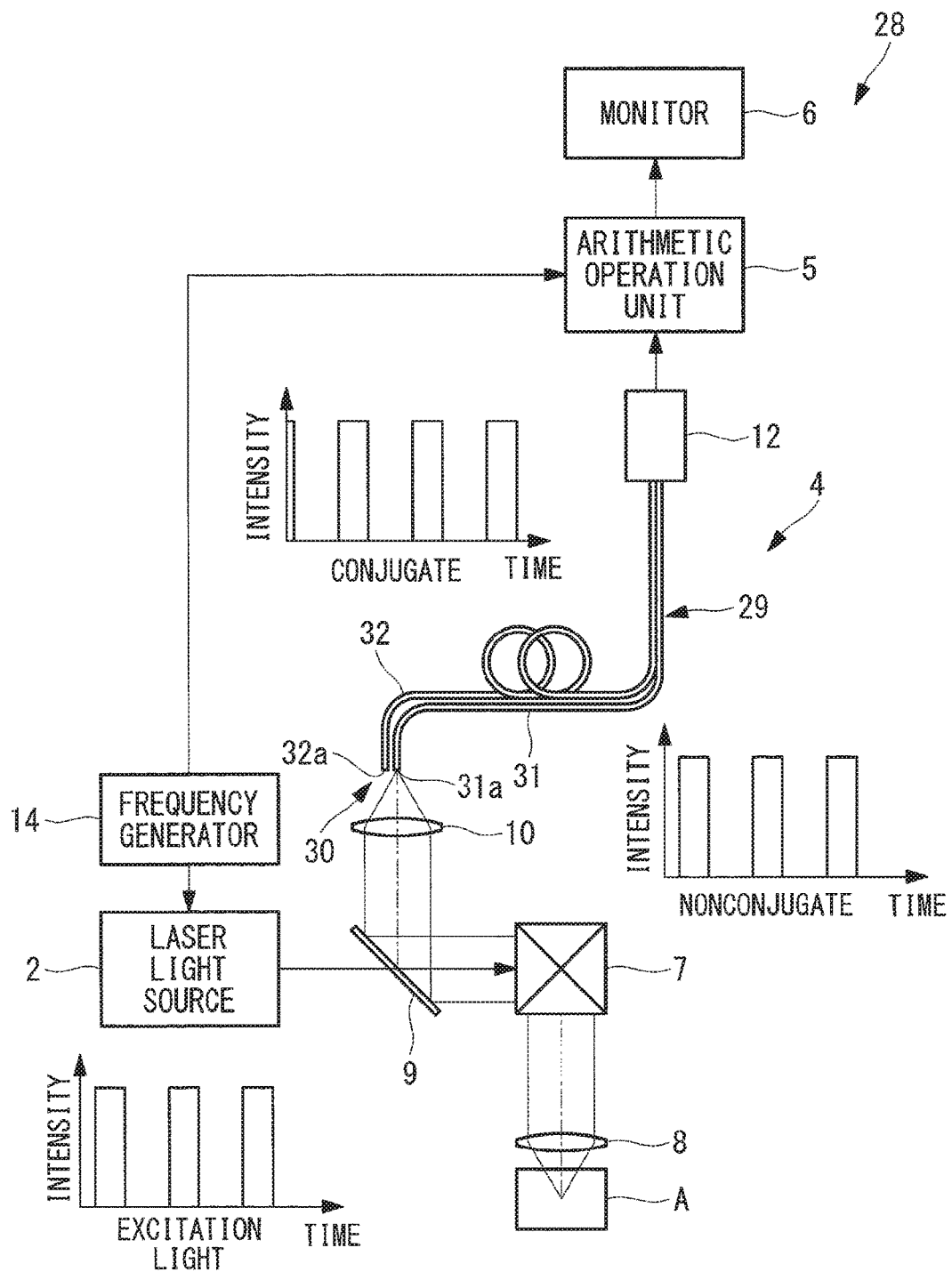
FIG. 8 is an overall configuration diagram showing a microscope according to a third embodiment of the present invention.

More specifically, in this embodiment, the setting unit 29 is composed of two optical fibers (setting units) 31 and 32 that are disposed between the image-forming lens 10 and the photodetector 12 and that have different lengths, as show in FIG. 8. In addition, the light-blocking member 30 is composed of one-side ends (incident ends) 31a and 32a of the two optical fibers 31 and 32.

The one end 31a of the first optical fiber 31 is disposed at a position coinciding with the image-forming position of fluorescence through the image-forming lens 10. On the other hand, the one end 32a of the second optical fiber 32 is disposed at a position shifted in a direction intersecting the optical axis of the fluorescent light beam relative to the image-forming position of fluorescence through the image-forming lens 10.

Each of the other ends of the two optical fibers 31 and 32 is disposed at a position that allows the propagating fluorescence to be made incident upon the same photodetector 12.

According to the microscope 28 of this embodiment with the above-described structure, the one end 31a of the first optical fiber 31 is disposed at a position coinciding with the image-forming position of fluorescence through the image-forming lens 10, and hence the incident end 31a of the first optical fiber 31 and the focusing point of excitation light in the sample A form optically conjugate positions. On the other hand, the incident end 32a of the second optical fiber 32 and the focusing point of excitation light in the sample A form optically nonconjugate positions.

As a result of the two optical fibers 31 and 32 being made to have different lengths, the fluorescence made to pass via the longer second optical fiber 32 is detected by the photodetector 12 at a later time than the fluorescence made to pass via the first optical fiber 31.

More specifically, this embodiment affords an advantage in that the setting unit 29 can be formed of two optical fibers 31 and 32 that are fixed and that have different lengths and can be made compact at low cost without having to use large-scale switching units, such as the movable mirror 13 and the acousto-optic deflector 16 or the free-space optical system 23. Although it is preferable that multimode fibers with high coupling efficiency be used for the optical fibers 31 and 32, the optical fibers 31 and 32 are not limited to those multimode fibers.

Figure 9:
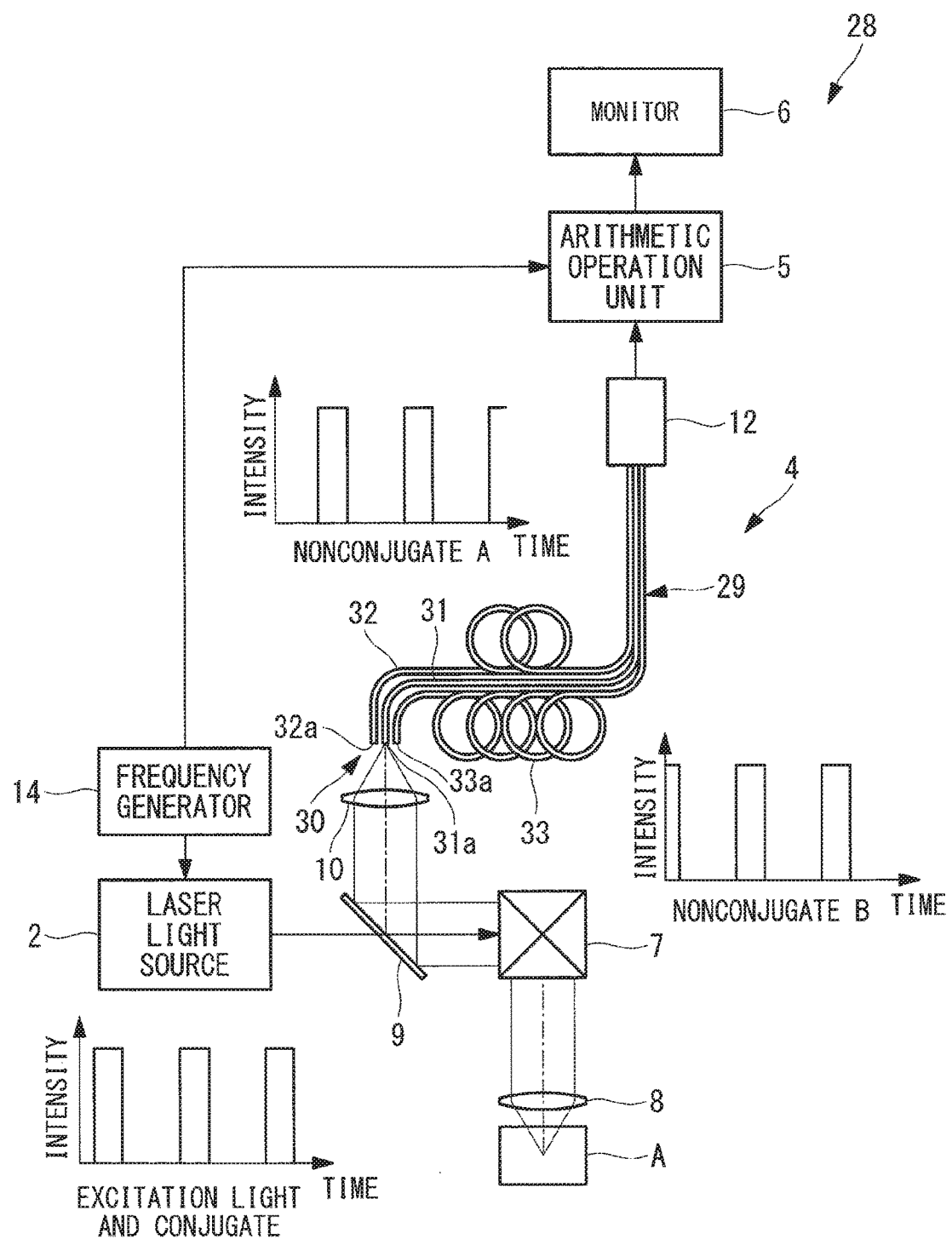
FIG. 9 is an overall configuration diagram showing a first modification of the microscope in FIG. 8.

In addition, although the two optical fibers 31 and 32 having different lengths are used in this embodiment, alternatively three or more optical fibers (setting units) 31, 32, and 33 having different lengths may be used as shown in FIG. 9, so that types of fluorescence may be acquired individually in a state where two or more of those optical fibers have an optically nonconjugate positional relationship, and subsequently the acquired types of fluorescence may be averaged. Through averaging, the noise of the types of fluorescence acquired in a nonconjugate positional relationship can be reduced.

Figure 10:
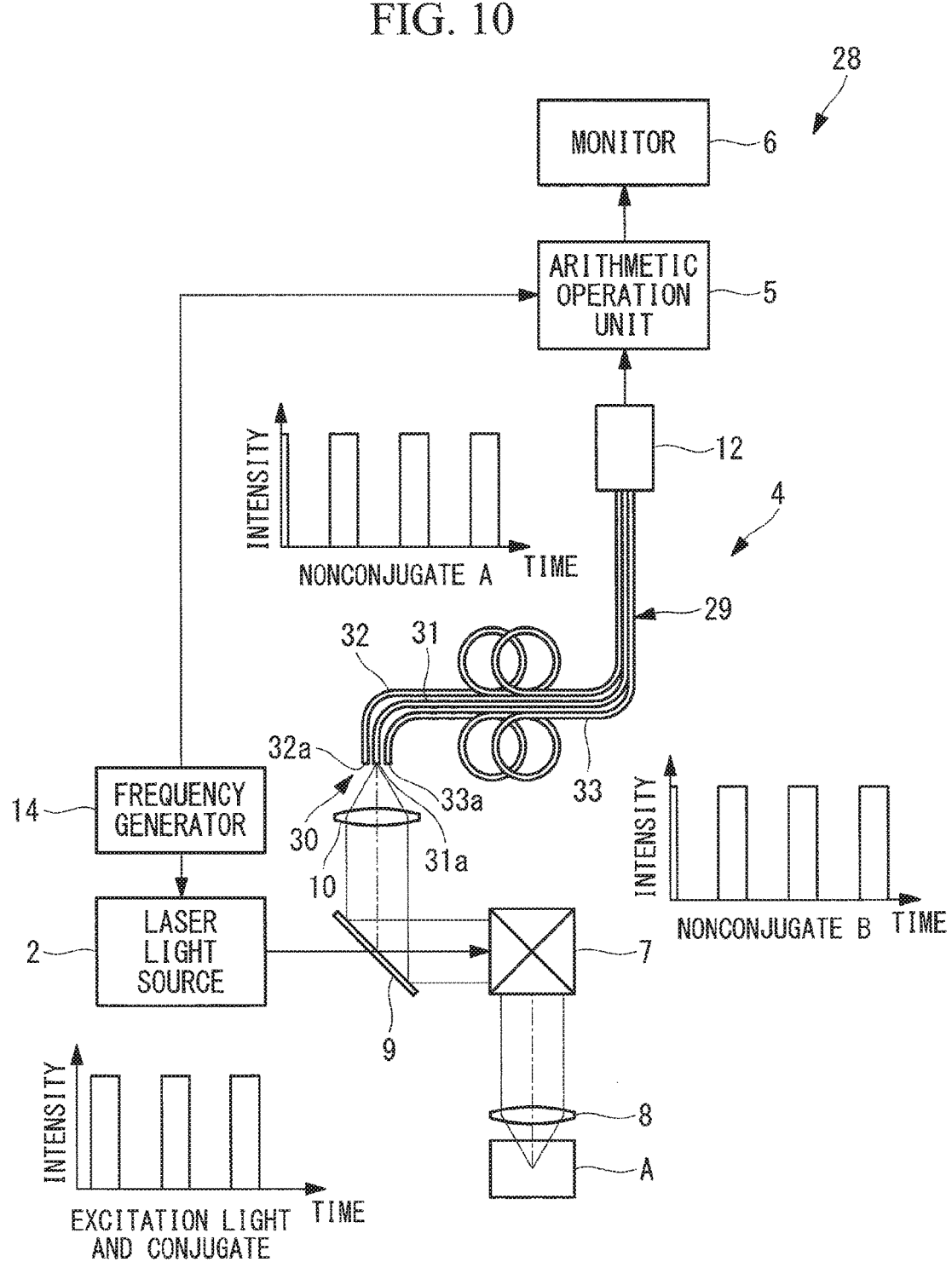
FIG. 10 is an overall configuration diagram showing a second modification of the microscope in FIG. 8.

In addition, as shown in FIG. 10, three or more optical fibers 31, 32, and 33 may be used, so that the length of the one optical fiber 31, which has a conjugate positional relationship for fluorescence detection, and the lengths of the other two or more optical fibers 32 and 33 may be made different from each other, and types of fluorescence passing via the two or more optical fibers 32 and 33 in an optically nonconjugate positional relationship may be simultaneously acquired and averaged. In this case, the light-blocking member 30 is formed of the one-side ends (incident ends) 31a, 32a, an 33a of the three optical fibers 31, 32, and 33.

In addition, although the difference between the types of fluorescence acquired by the photodetector 12 is calculated for each pixel in each of the above-described embodiments, this difference may be calculated for each image.

In addition, although subtraction is performed by the lock-in amplifier in the form of hardware in the arithmetic operation unit 5, instead of this, the difference may be calculated by composing the arithmetic operation unit 5 of a computer and using software such as signal processing.

In addition, in the first embodiment and the second embodiment, types of fluorescence may also be acquired in a plurality of optically nonconjugate positional relationships and then may be averaged, in the same manner as in the modification of the third embodiment.

As a result, the above-described embodiments lead to the following aspects.

One aspect of the present invention is a microscope including: a scanner for scanning excitation light from a light source; an objective optical system that focuses the excitation light scanned by the scanner onto a sample and that collects fluorescence generated by the sample at each scanning position; a light-blocking member that transmits a portion of the fluorescence collected by the objective optical system and that blocks another portion; a detector for detecting the fluorescence having passed through the light-blocking member; a setting unit that sets a positional relationship between the position of an opening in the light-blocking member and the focal point of the objective optical system in the sample to an optically conjugate positional relationship, in which in-focus fluorescence emitted from the focal point passes through the light-blocking member in an optical path from the sample to the detector, and to an optically nonconjugate positional relationship, in which the in-focus fluorescence does not pass through the light-blocking member, and that causes the detector to detect, at different times, types of fluorescence having passed through the light-blocking member in the set two types of positional relationships; and an arithmetic operation unit for calculating the difference between the fluorescence signals acquired by the detector at the different times.

According to this aspect, as a result of excitation light from the light source being scanned by the scanner and being focused by the objective optical system onto the sample, a fluorescent substance is excited at the focusing point of the excitation light in the sample, thereby generating fluorescence. After the generated fluorescence has been collected by the objective optical system, a portion of the fluorescence having passed through the light-blocking member is detected by the detector, and a fluorescence image is generated by associating the intensity of the detected fluorescence with the scanning position.

In this case, in a case where the operation of the setting unit causes the positional relationship between the position of the opening in the light-blocking member provided upstream of the detector and the focal point of the objective optical system in the sample to hold an optically conjugate positional relationship, both in-focus fluorescence and out-of-focus fluorescence are detected by the detector. In contrast, in a case where the operation of the switching unit causes the positional relationship between the light-blocking member and the focal point of the objective optical system in the sample to hold an optically nonconjugate positional relationship, in-focus fluorescence cannot pass through the light-blocking member, and hence only out-of-focus fluorescence is detected by the detector. These types of fluorescence are temporally separated by the setting unit and detected by the same detector at different times. Thereafter, as a result of the difference between these fluorescence signals being calculated by the arithmetic operation unit, in-focus fluorescence, from which out-of-focus fluorescence has been removed, can be captured, thereby acquiring a sharp fluorescence image.

In the above-described aspect, the setting unit may relatively move the position of the light-blocking member and the position of a fluorescence light beam that comes from the sample and that is incident upon the light-blocking member.

By doing so, an optically conjugate positional relationship and an optically nonconjugate positional relationship can be easily set as the positional relationship between the position of the opening in the light-blocking member and the focal point of the objective optical system in the sample. Here, the position of the fluorescence light beam includes both a position in a direction intersecting the optical axis of the fluorescence light beam and a position in a direction along the optical axis of the fluorescence light beam.

In addition, in the above-described aspect, the setting unit may relatively move, in a direction intersecting an optical axis of the fluorescence light beam, the position of the light-blocking member and the position of the fluorescence light beam incident upon the light-blocking member.

By doing so, when the focal position of the fluorescence light beam is made to coincide with the position of the opening in the light-blocking member, the positional relationship between the position of the opening in the light-blocking member and the focusing point of the excitation light in the sample can hold an optically conjugate positional relationship. On the other hand, when the focal position of the fluorescence light beam is disposed so as to be shifted in a direction intersecting the optical axis relative to the position of the opening in the light-blocking member, the positional relationship between the position of the opening in the light-blocking member and the focusing point of the excitation light in the sample can hold an optically nonconjugate positional relationship.

In addition, in the above-described aspect, the light source may modulate the excitation light in an arbitrary repeated waveform, and the setting unit may include a free-space optical system that splits the fluorescence collected by the objective optical system into a plurality of optical paths having different optical-path lengths and that causes each type fluorescence to be incident upon different positions of the light-blocking member.

By doing so, as a result of blinking excitation light emitted from the light source being focused onto the sample, blinking fluorescence generated by the sample is collected by the objective optical system and is incident upon the free-space optical system. The fluorescence incident upon the free-space optical system is split into a plurality of optical paths having different optical-path length, and types of fluorescence are then incident upon different positions of the light-blocking member.

In this manner, by providing a temporal delay by means of a long optical path, not only can the types of fluorescence be made to reach the light-blocking member at different times, but also it is possible to switch between a state where the position of the opening in the light-blocking member and the focusing point in the sample have an optically conjugate positional relationship and a state where these positions have an optically nonconjugate positional relationship. In short, in-focus fluorescence can be detected with even higher accuracy by using in-focus fluorescence and out-of-focus fluorescence generated by the sample at the same time.

In addition, in the above-described aspect, the light source may modulate the excitation light in an arbitrary repeated waveform, and the setting unit may include a light-beam moving unit for moving the fluorescence light beam in a direction intersecting the optical axis thereof.

In this manner, by moving the fluorescence light beam in a direction intersecting the optical axis through the operation of the light-beam moving unit, fluorescence can be made incident upon different positions of the light-blocking member at different times.

In addition, in the above-described aspect, the light-beam moving unit may be a deflection element capable of changing a deflection angle.

In this manner, by changing, through the operation of the deflection element, the deflection angle of the fluorescence light beam due to the deflection element, the fluorescence light beam can be easily moved in a direction intersecting the optical axis.

In addition, in the above-described aspect, the light-beam moving unit may be an acousto-optic element or an electro-optical element.

In this manner, by switching the voltage to be applied to the acousto-optic element or the electro-optical element, the exit angle of the fluorescence light beam can be changed, thereby making it possible to easily move the fluorescence light beam in a direction intersecting the optical axis.

In addition, in the above-described aspect, the light-blocking member may include a plurality of pinholes arrayed in a direction intersecting the optical axis of the fluorescence light beam and may be provided so as to be movable in the direction in which the pinholes are arrayed.

In this manner, by moving the light-blocking member in the direction in which the pinholes are arrayed, instead of moving the fluorescence light beam, it is possible to easily switch between an optically conjugate positional relationship, in which the image-forming position of fluorescence coincides with a pinhole, and an optically nonconjugate positional relationship, in which the image-forming position of fluorescence is shifted from the pinholes.

In addition, in the above-described aspect, the setting unit may relatively move, in the optical-axis direction of the fluorescence light beam, the position of the light-blocking member and an image-forming position of the fluorescence light beam incident upon the light-blocking member.

By doing so, when the image-forming position of the fluorescence light beam is made to coincide with the position of the opening in the light-blocking member, the positional relationship between the position of the opening in the light-blocking member and the focusing point of the excitation light in the sample can be made to hold an optically conjugate positional relationship. On the other hand, when the image-forming position of the fluorescence light beam is disposed so as to be shifted in the optical-axis direction relative to the position of the opening in the light-blocking member, the positional relationship between the position of the opening in the light-blocking member and the focusing point of the excitation light in the sample can be made to hold an optically nonconjugate positional relationship.

In addition, in the above-described aspect, the light source may modulate the excitation light in an arbitrary repeated waveform, and the setting unit may include a free-space optical system that splits the fluorescence collected by the objective optical system into a plurality of optical paths having different optical-path lengths and that causes the image-forming positions of the fluorescence light beam to differ.

By doing so, the types of fluorescence that have been split into different optical paths when incident upon the free-space optical system are made temporally distinct due to the difference in optical-path length and are incident upon the light-blocking member with different focal positions while passing through the optical paths. When the image-forming position of fluorescence having passed through one optical path coincides with the position of the opening in the light-blocking member, an optically conjugate positional relationship holds. When the image-forming position of fluorescence having passed through the other optical path is shifted in the optical-axis direction relative to the light-blocking member, an optically nonconjugate positional relationship holds.

In addition, in the above-described aspect, the setting unit may be an acousto-optic lens capable of changing the image-forming position of the fluorescence light beam.

In this manner, by switching the voltage to be applied to the acousto-optic lens, the focal position of the fluorescence light beam can easily be moved in the optical-axis direction.

In addition, in the above-described aspect, the light source may modulate the excitation light in an arbitrary repeated waveform, the setting unit may include a plurality of optical fibers that allow the fluorescence collected by the objective optical system to be incident thereon and that have different lengths, and the light-blocking member may be formed by disposing incident ends of the types of fluorescence upon the optical fibers such that the incident ends are arrayed in a direction intersecting the optical axis of a fluorescence light beam from the sample.

By doing so, blinking fluorescence generated by the sample is collected by the objective optical system, the optical fiber the incident end of which is disposed at the position optically conjugate with the focusing point of the excitation light in the sample transmits in-focus fluorescence and out-of-focus fluorescence, and the optical fiber the incident end of which is disposed at an optically nonconjugate position transmits out-of-focus fluorescence. These types of fluorescence that have passed through the optical fibers having different lengths are detected by the detector at different times due to a delay caused by the difference in length. By doing so, types of fluorescence having passed through different optical fibers can be separately detected by the same detector, and in-focus fluorescence can be separated and extracted with high accuracy, thereby making it possible to acquire a sharp image.

In addition, in the above-described aspect, the arithmetic operation unit may calculate the difference between two types of images generated by the fluorescence signals acquired by the detector in the two types of positional relationships set by the setting unit.

In addition, in the above-described aspect, the arithmetic operation unit may calculate, for each pixel, the difference between the fluorescence signals acquired by the detector in the two types of positional relationships set by the setting unit.

By doing so, because the difference between fluorescence signals acquired for each pixel at a short interval of time is calculated, a sharp image with less blurring can also be acquired even for a subject moving at high speed.

In addition, another aspect of the present invention is a microscope observation method for focusing, onto a sample through an objective optical system, excitation light scanned by a scanner, collecting, with the objective optical system, fluorescence generated by the sample at each scanning position, and detecting, with a detector, fluorescence having passed through a light-blocking member, the method including: a first step of detecting fluorescence with the detector in a state where the positional relationship between the position of an opening in the light-blocking member and a focal point of the objective optical system in the sample holds an optically conjugate positional relationship, in which in-focus fluorescence emitted from the focal point passes through the light-blocking member; a second step of detecting fluorescence with the detector at a different time from a time in the first step in a state where the positional relationship between the position of the opening in the light-blocking member and the focal point of the objective optical system in the sample holds an optically nonconjugate positional relationship, in which the in-focus fluorescence does not pass through the light-blocking member; and a third step of subtracting a fluorescence signal detected by the detector in the second step from a fluorescence signal detected by the detector in the first step.

The present invention affords an advantage in that out-of-focus fluorescence emitted from a sample can be detected with high accuracy, and the out-of-focus fluorescence can be removed from the detected fluorescence, thereby making it possible to acquire a sharp fluorescence image.

REFERENCE SIGNS LIST 1, 22, 28 Microscope
2 Laser light source (light source)
3 Switching unit (setting unit)
5 Arithmetic operation unit
7 Scanner
8 Objective lens (objective optical system)
11 Pinhole (light-blocking member)
12 Photodetector (detector)
13 Movable mirror (deflection element, light-beam moving unit)
16 Acousto-optic deflector (acousto-optic element, light-beam moving unit)
17 Electro-optical deflector (electro-optical element, light-beam moving unit)
18 Disc (light-blocking member)
19 Pinhole
21 Acousto-optic lens (setting unit)
23 Free-space optical system (setting unit, switching unit)
30 Light-blocking member
31, 32, 33 Optical fiber (setting unit)
A Sample

The invention claimed is:

1. A microscope comprising:
a scanner for scanning excitation light from a light source;
an objective optical system that focuses the excitation light scanned by the scanner onto a sample and that collects fluorescence generated by the sample at each scanning position;
a light-blocking member that transmits a portion of the fluorescence collected by the objective optical system and that blocks another portion;
a detector for detecting the fluorescence having passed through the light-blocking member;
a setting unit that sets a positional relationship between the position of an opening in the light-blocking member and a focal point of the objective optical system in the sample to an optically conjugate positional relationship, in which in-focus fluorescence emitted from the focal point passes through the light-blocking member in an optical path from the sample to the detector, and to an optically nonconjugate positional relationship, in which the in-focus fluorescence does not pass through the light-blocking member, and that causes the detector to detect, at different times, types of fluorescence having passed through the light-blocking member in the set two types of positional relationships; and
an arithmetic operation unit for calculating the difference between fluorescence signals acquired by the detector at the different times.

2. The microscope according to claim 1, wherein the setting unit relatively moves the position of the light-blocking member and the position of a fluorescence light beam that comes from the sample and that is incident upon the light-blocking member.

3. The microscope according to claim 2, wherein the setting unit relatively moves, in a direction intersecting an optical axis of the fluorescence light beam, the position of the light-blocking member and the position of the fluorescence light beam incident upon the light-blocking member.

4. The microscope according to claim 3,
wherein the light source modulates the excitation light in an arbitrary repeated waveform, and
the setting unit includes a free-space optical system that splits the fluorescence collected by the objective optical system into a plurality of optical paths having different optical-path lengths and that causes the types of fluorescence to be incident upon different positions of the light-blocking member.

5. The microscope according to claim 3,
wherein the light source modulates the excitation light in an arbitrary repeated waveform, and
the setting unit includes a light-beam moving unit for moving the fluorescence light beam in a direction intersecting the optical axis thereof.

6. The microscope according to claim 5, wherein the light-beam moving unit is a deflection element capable of changing a deflection angle.

7. The microscope according to claim 5, wherein the light-beam moving unit is an acousto-optic element or an electro-optical element.

8. The microscope according to claim 3, wherein the light-blocking member includes a plurality of pinholes arrayed in a direction intersecting the optical axis of the fluorescence light beam and is provided so as to be movable in the direction in which the pinholes are arrayed.

9. The microscope according to claim 2, wherein the setting unit relatively moves, in the optical-axis direction of the fluorescence light beam, the position of the light-blocking member and an image-forming position of the fluorescence light beam incident upon the light-blocking member.

10. The microscope according to claim 9,
wherein the light source modulates the excitation light in an arbitrary repeated waveform, and
the setting unit includes a free-space optical system that splits the fluorescence collected by the objective optical system into a plurality of optical paths having different optical-path lengths and that causes the image-forming positions of the fluorescence light beam to differ.

11. The microscope according to claim 9, wherein the setting unit is an acousto-optic lens capable of changing the image-forming position of the fluorescence light beam.

12. The microscope according to claim 1,
wherein the light source modulates the excitation light in an arbitrary repeated waveform,
the setting unit includes a plurality of optical fibers that allow the fluorescence collected by the objective optical system to be incident thereon and that have different lengths, and
the light-blocking member is formed by disposing incident ends of the types of fluorescence upon the optical fibers such that the incident ends are arrayed in a direction intersecting the optical axis of a fluorescence light beam from the sample.

13. The microscope according to claim 1, wherein the arithmetic operation unit calculates the difference between two types of images generated by the fluorescence signals acquired by the detector in the two types of positional relationships set by the setting unit.

14. The microscope according to claims 1, wherein the arithmetic operation unit calculates, for each pixel, the difference between the fluorescence signals acquired by the detector in the two types of positional relationships set by the setting unit.

15. A microscope observation method for focusing, onto a sample through an objective optical system, excitation light scanned by a scanner, collecting, with the objective optical system, fluorescence generated by the sample at each scanning position, and detecting, with a detector, fluorescence having passed through a light-blocking member, the method comprising:
a first step of detecting fluorescence with the detector in a state where the positional relationship between the position of an opening in the light-blocking member and the focal point of the objective optical system in the sample holds an optically conjugate positional relationship, in which in-focus fluorescence emitted from the focal point passes through the light-blocking member;
a second step of detecting fluorescence with the detector at a different time from a time in the first step in a state where the positional relationship between the position of the opening in the light-blocking member and the focal point of the objective optical system in the sample holds an optically nonconjugate positional relationship, in which the in-focus fluorescence does not passes through the light-blocking member; and
a third step of subtracting a fluorescence signal detected by the detector in the second step from a fluorescence signal detected by the detector in the first step.

* * * * *